(12) United States Patent
Harlan

(10) Patent No.: US 6,935,862 B2
(45) Date of Patent: Aug. 30, 2005

(54) DENTAL PROSTHESIS FABRICATION AND PLACEMENT SYSTEM AND ASSOCIATED METHODS

(76) Inventor: Laurence Harlan, 185 Honey Belle Oval, Chagrin Falls, OH (US) 44022

( * ) Notice: Subject to any disclaimer, the term of this patent is extended or adjusted under 35 U.S.C. 154(b) by 77 days.

(21) Appl. No.: 10/349,460

(22) Filed: Jan. 22, 2003

(65) Prior Publication Data

US 2004/0142305 A1 Jul. 22, 2004

(51) Int. Cl.[7] ................................................. A61C 5/08
(52) U.S. Cl. ...................................... 433/218; 433/223
(58) Field of Search .................................. 433/218, 219, 433/223, 215, 202.1

(56) References Cited

U.S. PATENT DOCUMENTS

| | | | |
|---|---|---|---|
| 3,861,044 A | 1/1975 | Swinson, Jr. | |
| 4,203,515 A | 5/1980 | Kahn et al. | |
| 4,504,230 A | 3/1985 | Patch | |
| 4,678,435 A | * 7/1987 | Long | ............ 433/218 |
| 5,192,207 A | 3/1993 | Rosellini | |
| 5,314,335 A | 5/1994 | Fung | |
| 5,487,663 A | * 1/1996 | Wilson | ............ 433/218 |
| 5,775,913 A | * 7/1998 | Updyke et al. | ............ 433/223 |
| 5,984,682 A | 11/1999 | Carlson | |
| 6,068,481 A | 5/2000 | Worthington | |
| 6,257,892 B1 | 7/2001 | Worthington | |
| 2001/0036618 A1 | 11/2001 | Worthington | |
| 2002/0045678 A1 | * 4/2002 | Lopez et al. | ............ 523/116 |
| 2002/0198285 A1 | * 12/2002 | Sang et al. | ............ 523/118 |

* cited by examiner

*Primary Examiner*—Melba Bumgarner
(74) *Attorney, Agent, or Firm*—Allen, Dyer, Doppelt, Milbrath & Gilchrist, P.A.

(57) ABSTRACT

A dental prosthesis fabrication and placement method is adapted for completion in one appointment. The dental prosthesis, such as a crown or short-span bridge, is a prefabricated composite shell that is modified by the addition of composite material and cured on-site to form a custom-modified device.

41 Claims, 3 Drawing Sheets

DENTAL PROSTHESIS FABRICATION AND PLACEMENT SYSTEM AND ASSOCIATED METHODS

BACKGROUND OF THE INVENTION

1. Field of the Invention

The present invention relates to systems and methods for performing a dental procedure, and, more particularly, to such systems and methods for fabricating and placing a dental crown or bridge.

2. Description of Related Art

The fabrication and placement of dental prostheses such as crowns and bridges typically requires at least two visits to the dentist's office to complete. At the first visit, the placement site in the patient's mouth is prepared, and a mold is made from which a permanent prosthesis is to be constructed. A temporary prosthesis is inserted into the site, awaiting the fabrication of the permanent device, which is usually performed at a remote location from the dentist's office. At a second visit, the permanent prosthesis is affixed into the site.

SUMMARY OF THE INVENTION

The present invention is directed to a dental prosthesis fabrication and placement system and associated methods that can be completed in one visit. The dental prosthesis, which may comprise, for example, a crown or short-span bridge, is a prefabricated composite shell that is modified by the addition of composite material and cured on-site to form a custom-modified device.

The method of the invention, which is for fabricating and placing a dental prosthesis, comprises the steps of placing a prefabricated prosthesis shell over a tooth that has a surface that has been prepared for prosthesis placement and trimming the shell to achieve desired seating on the tooth and optimal occlusion. The shell is then removed from the tooth, and the tooth's prepared surface is painted with a separating medium. An interior surface of the shell is painted with a bonding agent, and an uncured composite material is added to the shell's interior space.

Next the shell is positioned over the tooth, and the composite material is partially light cured in situ. The shell is removed from the tooth and modified as desired to achieve optimal conformation. Any added composite is then fully light cured, and the shell is affixed to the tooth.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 4A, a side view; FIG. 4B, an occlusal view; and FIG. 4C, an internal view.

DETAILED DESCRIPTION OF THE PREFERRED EMBODIMENTS

Figure 1:
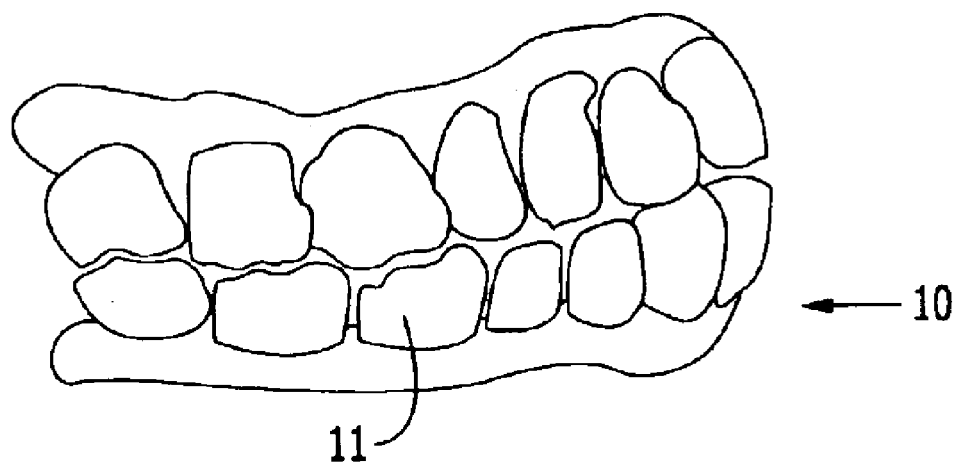
FIG. 1 is a side view of a model of the patient's mouth.
Figure 2:
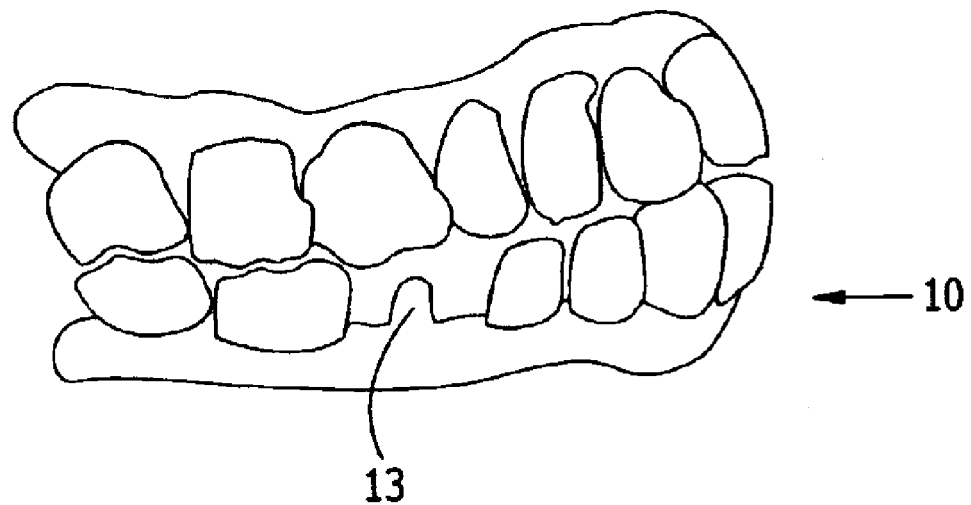
FIG. 2 is a side view of the model with the respective tooth prepared.
Figure 3:
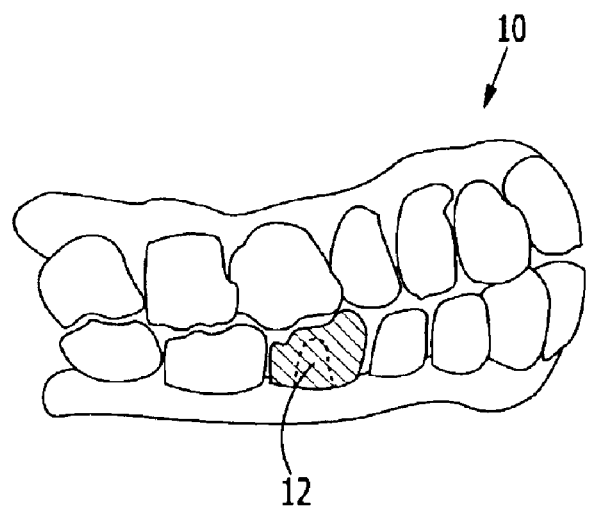
FIG. 3 is a side view of the model with a shell crown placed therein.
Figure 4A:
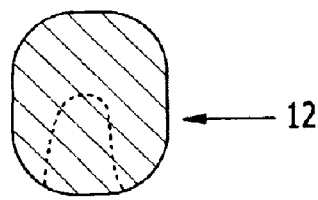
FIGS. 4A–4C are views of the shell crown.
Figure 4B:
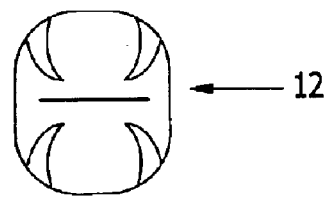
Figure 4C:
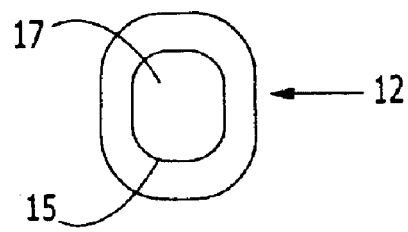
Figures 5, 6, 7, 8:
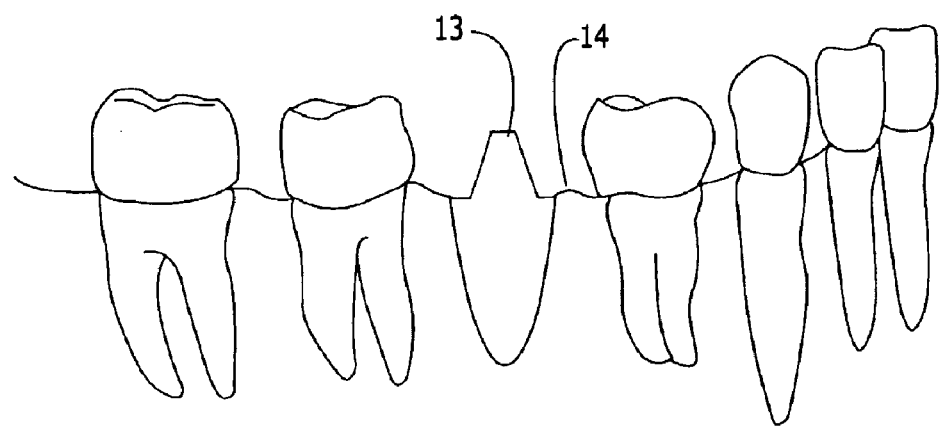
FIG. 5 is a side view of the mouth with the tooth to be crowned prepared.
FIG. 6 is a side view of the shell crown placed over the prepared tooth.
FIG. 7 is a side view of the shell crown having added material.
FIG. 8 is a side view of the finished crown bonded to the tooth.

A description of the preferred embodiments of the present invention will now be presented with reference to FIGS. 1–8.

The method of the present invention in a preferred embodiment comprises the steps of making a study model 10 of the patient's mouth (FIG. 1), comprising, for example, stone. This may be accomplished at an appointment prior to the prosthesis-placement appointment. Additional information that should be gathered include bite registrations and shade data. Using the study model 10 and additional information, the selected tooth 11 (or teeth) is prepared on the model in advance (FIG. 2) for fitting a custom shell restoration 12 thereto. The custom shell restoration 12 should be prepared to accurately reflect parameters such as color, as well as conformational parameters such as occlusion, proper contours, estimated gingival finish line, and interproximal contacts (FIGS. 3 and 4A–4C), and has in a preferred embodiment a minimum thickness of 0.3 mm and a preferred thickness of 1.0–1.5 mm.

The shell 12 may comprise, for example, a polyacrylic glass composite such as manufactured by Ceramco, Inc. (division of Dentsply International), under the name Cristobol. This material is not intended as a limitation, and other composite compounds exhibiting appropriate handling and wear characteristics, such as Sculpture, BelleGlass, AtrGlass, and Targis, may be substituted by one of skill in the art without departing from the spirit of the present invention. Such materials are processed or polymerized by various combinations of light activation, heat, pressure, and vacuum.

In an alternative embodiment for a single crown, a kit is provided comprising a variety of standardized size and shade premanufactured crown shells.

At the treatment appointment the patient is anesthetized, and the tooth 13 (teeth) to be treated is prepared by a method as known in the art, including preparing the tooth 13 with a shoulder or prominent chamfer gingival margin. In a preferred embodiment old amalgam and bases are removed. Also in a preferred embodiment, the present technique is not used for single crowns posterior to the first molar and for bridges posterior to the second bicuspid. A bridge should preferably span no more than three teeth. Preferably all undercuts present in the prepared tooth 13 (teeth) are eliminated using an appropriate buildup or filler material. Hemostasis of the surrounding gingival tissue 14 is preferred. Gingival retraction cord should be trimmed and placed completely into the sulcus to achieve both retraction and hemostasis.

A backup system for making a temporary crown should preferably be in place should the procedure of the present invention not be successful.

Next the prefabricated crown or bridge shell 12 is placed over the prepared tooth 13 (or teeth) and trimmed to seat completely on the prepared tooth 13 (teeth) and to achieve optimal occlusion. The shell 12 should fit passively, yet completely, and should be checked to ensure that there are correct interproximal contacts. If the shell 12 does not fit completely, the tooth 13, the interproximal contacts, the gingival margins, and the internal aspect 15 of the shell 12 should be relieved as needed. If interproximal contacts are insufficient, they can be corrected later.

The shell 12 is removed from the mouth, the prepared surfaces of the tooth 13 (teeth) are painted with a separating medium, such as a thin coating of water-soluble lubricant. The internal aspect 15 of the shell 12 should be cleaned, etched and silinated if necessary, and painted with the appropriate bonding agent or adhesive. The interior 17 of the shell 12 should be filled approximately halfway, with a lining of soft uncured composite 16 placed over the adhesive (e.g., modeling compound and primer). Although it is preferable to use the same material for the direct reline as was used to construct the shell 12, the composite shell 12 is compatible with standard composites used in the art of posterior dental restorations.

The partially filled shell 12 is placed over the prepared tooth 13 (teeth) to establish the proper occlusion, and the gross excess composite that may establish undercuts with the adjacent teeth is removed. The composite 16 is light cured from the buccal, lingual, and occlusal aspects for no more than several seconds, typically approximately 5–10 seconds. The shell 12 is removed and inspected for the presence of voids, which are filled with small additions of uncured composite, and is again pressed into place over the prepared tooth 13 (teeth) and light cured.

This process is repeated as many times as necessary to develop a fully adaptive internal aspect with complete gingival integrity. If there are insufficient interproximal contacts, they may be modified in the same manner by bonding additional material to the external surface of the shell 12. Once the addition of material to the shell 12 has been completed, the modified shell 12 should be sufficiently polymerized to optionally harden the entire prosthesis by light curing for 6–10 minutes, preferably in a light curing oven.

Next the shell 12 is trimmed to establish proper contours and to eliminate any gingival margin overhangs. The occlusion should be checked and refined as needed, and the external surface should be polished using an instrument such as, but not intended to be limited to, diamond, carbide, and silicone polishing instruments.

A radiograph may be exposed to verify the accuracy of the fit. Prior to cementation, the internal aspect 15 of the shell is then microetched, silinated, and coated with an appropriate bonding agent. The prepared tooth 13 should be cleaned to remove all the separating medium, acid etched, usually with buffered phosphoric acid, and coated with the appropriate bonding agent. The retraction cord should be removed, and the crown 12 should be cemented with a dual-cure composite luting cement to achieve a fully bonded, single-appointment final restoration.

It should be noted that the laboratory-processed shell 12 is likely to be polymerized significantly more than the reline portion of the crown 16. It is this well-polymerized, most durable portion of the shell 12 that covers most of the tooth, thereby protecting stress areas and providing for minimal occlusal wear. The weakest area is the gingival margin, which should, at the very least, be as durable and provide the same integrity as the best direct composite restoration.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and methods illustrated and described herein are by way of example, and the scope of the invention is not limited to the exact details thereof.

What is claimed is:

1. A method for fabricating and affixing a dental prosthesis in a mouth of a patient comprising the steps of:

placing a prefabricated prosthesis shell over a tooth that has a surface that has been prepared for prosthesis placement;

trimming the shell to achieve desired seating on the tooth and optimal occlusion;

removing the shell from the tooth;

painting the tooth prepared surface with a separating medium;

painting an interior surface of the shell with a bonding agent;

adding an uncured composite material to an interior space of the shell;

positioning the shell over the tooth;

partially light curing the composite material in situ;

removing the shell from the tooth;

modifying the shell as desired to achieve optimal conformation;

fully light curing the composite material; and affixing the shell to the tooth.

2. The method recited in claim 1, further comprising the steps of:

making a model of a mouth of the patient;

preparing a tooth in the model mouth corresponding to the tooth for which the prosthesis is intended; and prefabricating the prosthesis shell commensurate with the prepared model tooth.

3. The method recited in claim 2, wherein the prefabricating step comprises reflecting at least one mouth conformation parameter selected from a group consisting of bite registration, occlusion, contour, gingival finish line, and interproximal contacts.

4. The method recited in claim 3, further comprising the step of determining a shade of the intended tooth, and wherein the prefabricating step further comprises preparing the prosthesis shell with a shade commensurate with the intended tooth shade.

5. The method recited in claim 1, wherein the shell has a thickness measured between an external surface and the interior surface in a range of 0.3–1.5 mm.

6. The method recited in claim 1, wherein the shell comprises a polyacrylic glass composite.

7. The method recited in claim 1, wherein the shell is selected from a plurality of premanufactured crown shells.

8. The method recited in claim 1, wherein the shell is selected from a group consisting of a single crown shell and a short-span bridge.

9. The method recited in claim 1, further comprising the step, prior to the placing step, of preparing the tooth with at least one of a shoulder and a prominent chamfer gingival margin.

10. The method recited in claim 9, wherein the preparing step further comprises removing extant amalgam and bases from the tooth.

11. The method recited in claim 9, wherein the preparing step further comprises eliminating any extant undercuts in the tooth.

12. The method recited in claim 1, further comprising the step, prior to the placing step, of achieving hemostasis of gingival tissue surrounding the tooth.

13. The method recited in claim 12, wherein the hemostasis achieving step comprises trimming gingival retraction cord and placing the cord into a sulcus of the mouth.

14. The method recited in claim 13, further comprising the step of removing the retraction cord prior to the shell affixing step.

15. The method recited in claim 1, further comprising the steps, following the placing and the trimming steps, and prior to the painting steps, of:

examining the fit of the shell to ensure correct interproximal contacts; and if the fit is incomplete, relieving the interproximal contacts, gingival margins, and an internal aspect of the shell as determined by the fit examining step.

16. The method recited in claim 1, wherein the separating medium comprises a water-soluble lubricant.

17. The method recited in claim 1, further comprising the steps, following the separating medium painting step, of cleaning the shell interior surface.

18. The method recited in claim 1, wherein the adding step comprises adding soft uncured composite material to a level of approximately half-full.

19. The method recited in claim 1, wherein the uncured composite material comprises a substantially same material as the prefabricated prosthesis shell.

20. The method recited in claim 1, further comprising the step, following the positioning step, of removing excess uncured composite material.

21. The method recited in claim 1, wherein the partially light curing step comprises light curing for approximately 5–10 seconds.

22. The method recited in claim 1, wherein the modifying step comprises filling any voids with uncured composite material, again positioning the shell over the tooth, and again partially light curing the composite material in situ.

23. The method recited in claim 1, wherein the shell modifying step comprises correcting for insufficient interproximal contacts by bonding additional composite material to an external surface of the shell.

24. The method recited in claim 1, wherein the fully light curing step comprises light curing for approximately 6–10 minutes in a light curing oven.

25. The method recited in claim 1, further comprising the step of trimming the fully light cured shell to establish desired contours and to eliminate any gingival margin overhang prior to the shell affixing step.

26. The method recited in claim 1, further comprising the step of polishing the fully light cured shell prior to the shell affixing step.

27. The method recited in claim 1, further comprising the step of taking a radiographic image of the shell in situ to verify an accuracy of the fit prior to the shell affixing step.

28. The method recited in claim 1, further comprising the steps of microetching and coating with a bonding agent the fully light cured shell prior to the shell affixing step.

29. The method recited in claim 1, further comprising the steps of cleaning, acid etching to remove separating medium, and coating with a bonding agent the prepared tooth prior to the shell affixing step.

30. A method of fabricating a dental prosthesis comprising the steps of:

trimming a prefabricated prosthesis shell to achieve desired seating on a tooth and optimal occlusion;

adding an uncured composite material to an interior space of the shell;

partially light curing the composite material;

modifying the shell as desired to achieve optimal conformation by filling any voids with uncured composite material and again partially light curing the composite material in situ; and fully light curing the composite material.

31. The method recited in claim 30, wherein the shell has a thickness measured between an external surface and the interior surface in a range of 0.3–1.5 mm.

32. The method recited in claim 30, further comprising the step, prior to the trimming step, of cleaning the shell interior surface.

33. The method recited in claim 30, wherein the shell comprises a polyacrylic glass composite.

34. The method recited in claim 30, wherein the shell is selected from a plurality of premanufactured crown shells.

35. The method recited in claim 30, wherein the shell is selected from a group consisting of a single crown shell and a short-span bridge.

36. The method recited in claim 30, further comprising the steps, following the trimming step, of cleaning, etching, and silinating the shell interior surface.

37. The method recited in claim 30, wherein the adding step comprises adding soft uncured composite to a level of approximately half-full.

38. The method recited in claim 30, wherein the partially light curing steps comprise light curing for approximately 5–10 seconds.

39. The method recited in claim 30, wherein the fully light curing step comprises light curing for approximately 6–10 minutes in a light curing oven.

40. The method recited in claim 30, further comprising the step of trimming the fully light cured shell to establish desired contours.

41. The method recited in claim 30, further comprising the step of polishing the fully light cured shell.

* * * * *